(12) United States Patent
Grady

(10) Patent No.: US 6,789,941 B1
(45) Date of Patent: Sep. 14, 2004

(54) DUAL C-ARM ANGIOGRAPHIC DEVICE FOR FLAT PANEL RECEPTOR

(76) Inventor: John K. Grady, 5 Park St., Ayer, MA (US) 01432

(*) Notice: Subject to any disclaimer, the term of this patent is extended or adjusted under 35 U.S.C. 154(b) by 64 days.

(21) Appl. No.: 10/155,539

(22) Filed: May 24, 2002

(51) Int. Cl.[7] .................................................. H05G 1/02
(52) U.S. Cl. ....................................... 378/197; 378/196
(58) Field of Search ................................ 378/195, 196, 378/197, 198

(56) References Cited

U.S. PATENT DOCUMENTS

| | | |
|---|---|---|
| 1,337,904 A | 4/1920 | Greville |
| 1,408,559 A | 3/1922 | Zulauf |
| 1,599,696 A | 9/1926 | Wantz |
| 2,890,349 A | 6/1959 | Huszar |
| 3,617,749 A | 11/1971 | Massiot |
| 3,892,967 A | 7/1975 | Grady et al. |
| 4,150,297 A | 4/1979 | Borggren |
| 4,358,856 A | 11/1982 | Stivender et al. |
| 4,365,343 A | 12/1982 | Grady et al. |
| 4,653,083 A | 3/1987 | Rossi |
| 4,802,197 A | 1/1989 | Juergens |
| 4,884,293 A | 11/1989 | Koyama |
| 4,961,214 A * | 10/1990 | Van Endschot et al. .... 378/197 |
| 4,987,585 A | 1/1991 | Kidd et al. |
| 5,450,466 A | 9/1995 | Kadowaki et al. |
| 5,515,416 A | 5/1996 | Siczek et al. |
| 6,031,888 A * | 2/2000 | Ivan et al. ..................... 378/20 |
| 6,264,364 B1 | 7/2001 | Pflaum et al. |
| 6,309,102 B1 | 10/2001 | Stenfors |
| 6,325,537 B1 | 12/2001 | Watanabe |
| 6,428,206 B1 * | 8/2002 | Watanabe ..................... 378/197 |
| 6,461,039 B1 * | 10/2002 | Klotz et al. .................. 378/197 |

* cited by examiner

Primary Examiner—Edward J. Glick
Assistant Examiner—Allen C. Ho
(74) Attorney, Agent, or Firm—Donald S. Holland, Esq.; Holland & Bonzagni, P.C.

(57) ABSTRACT

A dual C-arm angiographic device for flat panel x-ray receptor ("dual C-arm gantry") comprises: a base attached to the floor; an outer C-shaped track non-movably attached to the base; a crawler carriage that moves along the outer track; and a counterweighted, inner C-shaped instrument bracket ("inner C-arm") pivotally attached to the crawler carriage. A detector/counterweight housing, flat-panel x-ray receptor, and x-ray tube and collimator are attached to the inner C-arm. The bottom end of the outer track terminates at the base, such that the outer track arches over the side and top of a separate patient support table. Additionally, the outer track, crawler carriage, and inner C-arm are mutually configured such that the dual C-arm gantry is capable of full spherical angulation and of providing a full range of clinical positioning, while minimizing interference with clinical use patterns (i.e., the head end of the table is left clear for all angulations).

22 Claims, 13 Drawing Sheets

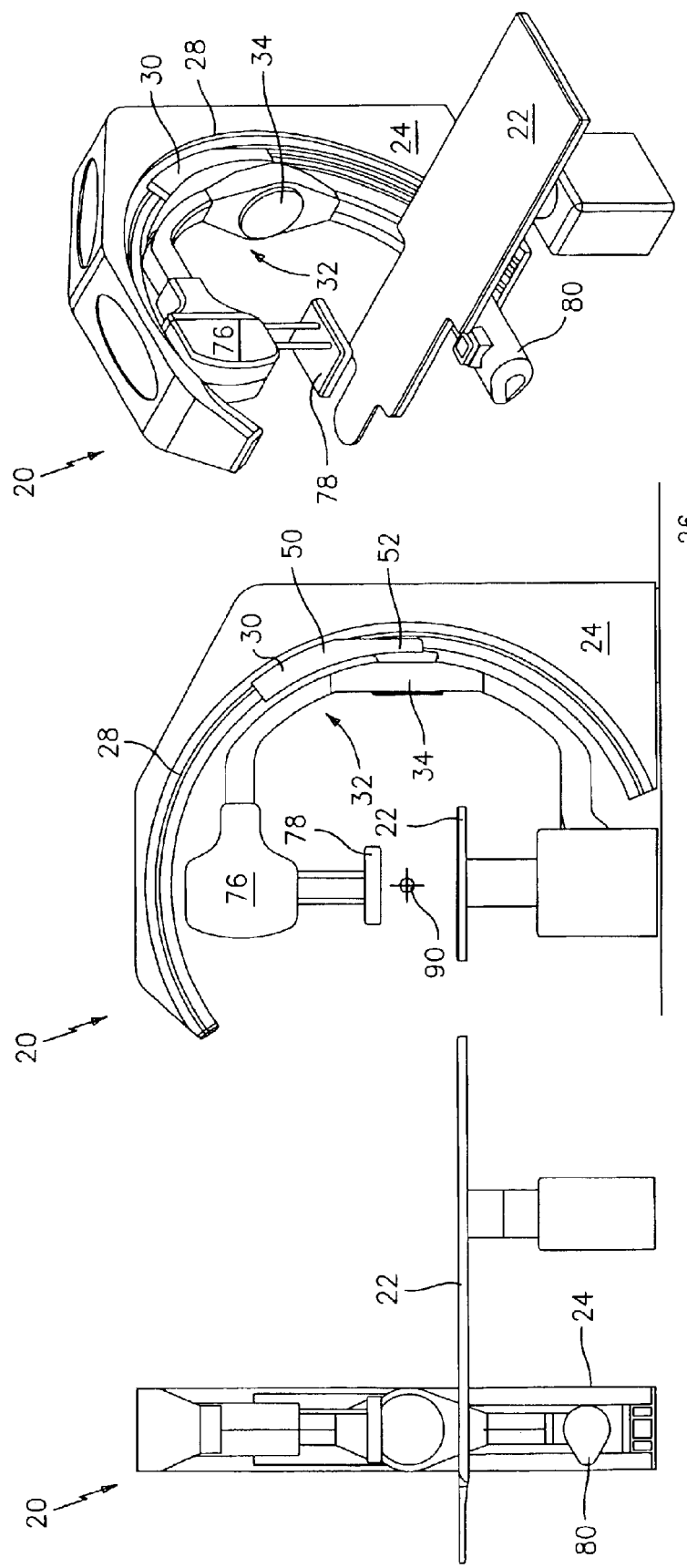

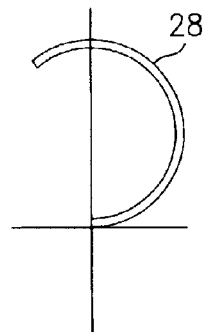
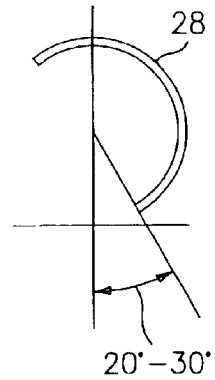
*FIG. 5C*     *FIG. 5D*
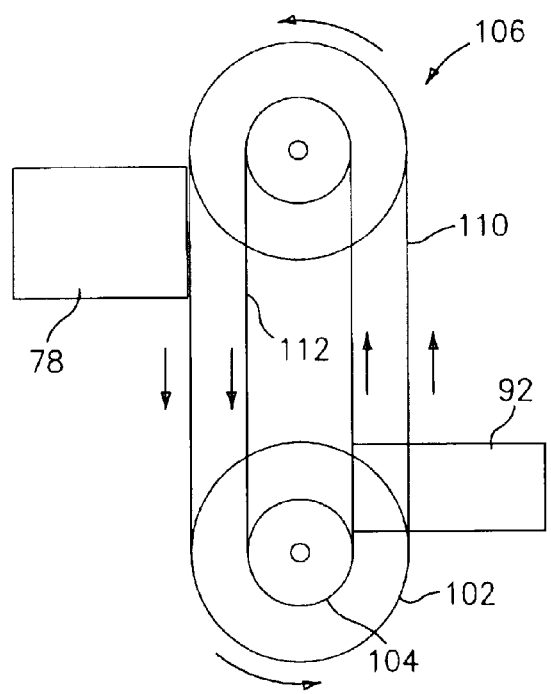
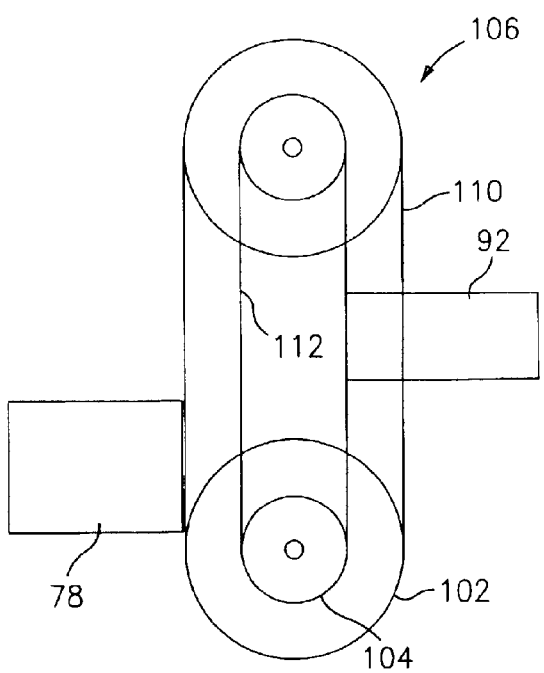
*FIG. 6D*     *FIG. 6E*

DUAL C-ARM ANGIOGRAPHIC DEVICE FOR FLAT PANEL RECEPTOR

FIELD OF THE INVENTION

The present invention relates to medical diagnostic equipment, and, more particularly, to apparatuses for supporting and positioning x-ray and other medical imaging devices.

BACKGROUND

Angiography involves the use of x-rays or other electromagnetic waves to examine arteries, veins, organs, and the like. Typically, a contrast agent (e.g., x-ray dye) is applied to the features under observation, via a catheter passing through the skin or an injection, to differentiate them from surrounding regions of the body. For most angiographic procedures, the x-rays being applied to a patient must be precisely directed, in order to ensure that the proper area is examined. Since orienting patients with respect to stationary x-ray devices (which typically include an x-ray source and an x-ray receptor) has been found to be imprecise, many gantry-like mechanisms have been developed over the years for supporting and positioning x-ray devices.

In designing x-ray support apparatuses, the x-ray device should ideally be positionable for use anywhere around the periphery of a patient in three dimensions. More specifically, it is typically desirable to utilize spherical angulation, where x-rays can be directed from any loci on an imaginary sphere centered on the patient to an isocenter of the x-ray device (the isocenter is the point of intersection of an axis defined by the x-ray source and receptor and the axis of angulation, i.e., the axis of device rotation). Other factors to take into account include: maintaining the x-ray beam normal to the x-ray receptor; the size of the examination room, and the room's ability to accommodate large devices; unrestricted access to the patient, especially around the head area; minimizing control complexity and/or the need for computer image correction or manipulation; and, as always, cost.

Most current x-ray device support apparatuses utilize either a parallelogram-shaped construct or a combination of C-, U-, and/or L-shaped arms for x-ray device positioning and (ideally) spherical angulation. An example of the former is shown in U.S. Pat. No. 3,892,967 to Grady et al. ("Grady"). In Grady, an x-ray source 23 and receptor 22 are positioned with respect to a patient P by way of an angularly-adjustable, pivoting, rotating parallelogram 3, 5, 8, 9. This achieves 360° rotation coverage about the patient P, by virtue of the parallelogram being rotatable about shaft 2, and 55° of head/foot tilt (the arms 8, 9 can be moved in and out). Thus, the device basically moves in an unrestricted way on the surface of a sphere about the patient, and the x-ray image itself inherently always remains "upright" irrespective of the compound angles used. However, to cover from head to foot on a six feet tall patient, the "throat depth" (clearance) of the support apparatus has to be over six feet. This makes the support apparatus at least ten to twelve feet long, plus the patient tabletop has to travel at least six feet, which means it must be eight to nine feet long. Thus, the entire system is almost twenty feet long, necessitating a twenty-eight or thirty foot long room, which might cause architectural problems.

Because parallelogram-based devices are so bulky, various C-arm based devices have been developed over the years. However, large C-arms are difficult to balance (a parallelogram can be an entirely mechanically-balanced device), since the entire mass of the C-shaped structure is offset to one side. Accordingly, these have primarily taken the form of a simple, light, balanced, C-shaped arm which holds the x-ray source at one end and the receptor at the other end. The C-shaped arm slides in a journal, and is positionable by way of one or more pivoting arms attached to the journal. Such devices can deliver most of the angular coverage of a parallelogram in a smaller space, but typically have several severe, inherent problems, such as the inability to carry heavy equipment without dangerous power-driven operation.

Furthermore, with existing C-arm based devices, as the axis of the x-ray beam approaches the horizontal, rotating the horizontal axis only serves to rotate the image, without changing the viewing angle. This results in zero image rotation with a vertical beam, and 100 percent rotation (only) at a horizontal beam. In between 0° and 90° the x-ray beam/positioner angular relationship is complex, and the two rotation axes interact. The result is a tilted image as viewed on the x-ray image screen. This effect can be compensated for by either mechanically rotating the x-ray receptor (and also the source collimator if a square x-ray field is utilized) according to a pre-programmed code, or by implementing an "image de-rotation" scheme where the image, as stored electronically, is manipulated by digital means. However, such systems are expensive, and can ultimately degrade the image.

There have been numerous variations in the design and construction of C-arm based x-ray gantries, but two main divisions are apparent: types where the horizontal C-arm axle comes at the patient from the left side, and types where the C-arm axle comes over the patient's head. In regards to the former, the achieved angle and tilting image problem is severe, plus the left side of the patient is obstructed. To solve that, putting the C-arm axle at the head of the patient gives good angular coverage, but the patient can only be imaged as far as the abdomen area, since otherwise the patient's head will hit the C-arm structure. The C-arm cannot be made larger in radius, as the center of rotation must be in the patient (isocentric operation is a requirement), and the floor and ceiling set bounds on the outer diameter of the C-arm, when the center of rotation is in the patient's body. Thus, "head end" mounting brings restricted coverage of the patient's length, especially below the abdomen.

U.S. Pat. No. 4,358,856 to Stivender et al. ("Stivender"), with reference to its FIG. 2, attempted to solve these problems by mounting a sliding, journal type C-arm 25 (with rotating axle construction) on a rotating, swinging, L-shaped member 10, where the lower right part of the "L," viewed as an alphabetical character, is attached to a bearing 14 centered under the isocenter 37. While this design provided good angular coverage, it presented its own problems. More specifically, the height or structural width of the horizontal member of the L-shaped arm 10 on the floor 15 effectively "raised the floor," requiring that the C-arm 25 have a smaller radius by about six inches. This is a critical shortcoming, as everything is much closer to the table and patient, due to the smaller "C" radius. Furthermore, swinging the L-shaped arm 10: (i) rotates the image yet again on another axis (now a three way interaction); and (ii) is problematic in a clinical sense, as it sweeps out a 90° arc to the left of the patient's head, where various monitors would normally be placed, medical lines are attached to the patient, and where nurses typically stand. As a result, units such as those shown in Stivender are almost always left at the head end of the patient (i.e., the L-shaped arm is not moved), mimicking other existing devices where a large radius C- or U-shaped arm is permanently mounted at the head.

U.S. Pat. No. 4,653,083 to Rossi ("Rossi"), with reference to its FIG. 1, discloses a C-arm based x-ray gantry with: a floor-mounted stand 1; an outer C-shaped track 8 attached to the stand; and an inner U-shaped arm 11 rotatably connected to a carriage 9 that slides along the outer track 8. While this device provides good angular coverage, it is very difficult to balance, and, therefore, was never commercially produced. More specifically, because the outer track 8, inner arm 11, and table T are all offset to one side of the stand 1, the stand has to be either provided with a large counterweight for balance, or the stand has to be particularly well secured to the floor. Furthermore, to balance the x-ray source X and receptor I, a counterweight (not shown) was required to be disposed in the vertical portion of the inner arm 11. This placed a large weight far off the x-ray beam axis and far from the isocenter C, leaving the whole inner arm 11 severely unbalanced with respect to the outer track and stand. Also, while the inner arm 11 was balanced about its pivot rotation axis 12, it required a large motor to crawl around the outer track 8.

Another problem associated with Rossi and similar designs is that they utilize cameras and image intensifier x-ray tubes (e.g., intensifier I in FIG. 1 in Rossi), resulting in a very tall and heavy assembly. Also, there is the possibility of the top of the image tube interfering with the outer C-arm or track when the image tube is moved axially away from the x-ray tube. Accordingly, the outer track must be quite large to accommodate the twelve- to sixteen-inch image intensifier tube, and still allow the inner C- or U-shaped arm to swing freely to compound angles without hitting the outer track.

Accordingly, it is a primary object of the present invention to provide a floor-mounted x-ray device support and positioning apparatus that achieves full spherical angulation, without image rotation, via ±90° transverse coverage across or around the patient's long axis.

Another primary object of the present invention is to provide an x-ray support apparatus that can be positioned to minimally interfere with clinical use patterns, including leaving the head end of a patient completely clear, for all projections of interest.

Another object of the present invention is to provide an x-ray support apparatus that is inherently stable, that can fit inside a normal-sized hospital room, and that does not require the installation of support buttresses or the like.

Still another object of the present invention is to provide an x-ray support apparatus that utilizes a flat panel x-ray receptor (thereby eliminating the need for an image intensifier lube), and that utilizes an improved counterweight system for properly balancing the flat panel receptor against a heavier x-ray source.

SUMMARY

A dual C-arm angiographic device for flat panel x-ray receptor ("dual C-arm gantry") comprises: a base attached to the floor; an outer C-shaped track non-movably attached to the base; a crawler carriage that moves along the outer track; and an inner C-shaped instrument bracket ("inner C-arm"), concentric with respect to the outer track, that is pivotally or rotatably attached (±180°) to the crawler carriage ((he inner C-arm is only rotatably attached to the crawler carriage, and does not slide within or with respect to the crawler carriage). A detector/counterweight housing and a flat-panel x-ray receptor, as well as an x-ray tube and collimator, are respectively attached to the ends of the inner C-arm. Also, the bottom end of the outer track terminates at the base, such that the outer track arches over a separate patient support table.

For positioning the inner C-arm, the crawler carriage (and hence the inner C-arm) can be moved ±90° by traversing from one end of the outer track to the other. However, the inner C-arm pivot point (the point on the crawler carriage at which the inner C-arm is pivotally connected) is circumferentially offset from the point at which the crawler carriage is movably attached to the outer track. This effectively allows the crawler carriage to "stick out" past the bottom end of the outer track, resulting in full spherical angulation and providing a full range of clinical positioning, while still allowing for the outer track to be "arched up" over the table. In other words, the circumferential offset allows the outer track to be placed where it interferes the least with clinical use patterns (specifically, on the side of a patient, away from the head).

The base may be provided with a linear bearing or roller track, slidably connected to a floor plate or carriage. This allows the base to be moved, e.g., towards or away from the patient support table For the dual C-arm gantry to work properly, the top and bottom of the inner C-arm must weigh approximately the same to balance it around the pivot point. Accordingly, a counterweight system is housed in the detector/counterweight housing. The counterweight system is used to provide a balancing weight to the x-ray source tube and collimator, which is typically much heavier than the flat-panel x-ray receptor, and to provide a balance for the receptor panel itself, which can be moved in and out (to bring it closer or further away from a patient).

The dual C-arm gantry can also be used for supporting and positioning other medical imaging or radiologic devices.

BRIEF DESCRIPTION OF THE DRAWINGS

These and other features, aspects, and advantages of the present invention will become better understood with respect to the following description, appended claims, and accompanying drawings, in which:

FIGS. 1A–1C show front elevation, side elevation, and perspective views, respectively, of a dual C-arm angiographic device for flat panel x-ray receptor ("dual C-arm gantry"), according to the present invention;

FIGS. 5C and 5D are schematic views illustrating the positioning of the outer C-shaped track portion of the dual C-arm gantry; and FIGS. 6A–6E are various views of an x-ray detector counterweight system according to the present invention.

DETAILED DESCRIPTION

Figure 1D:
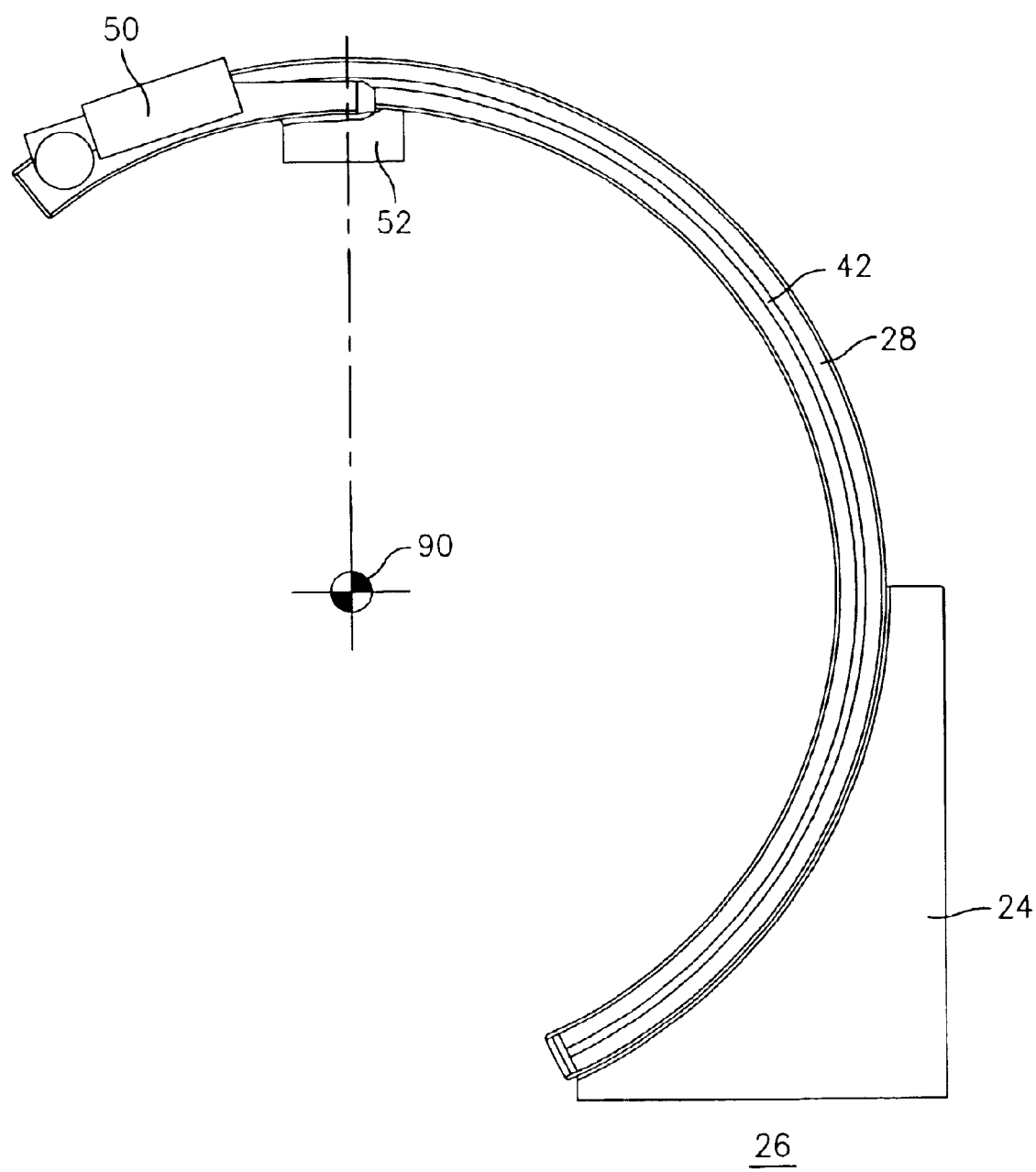
FIG. 1D is a side elevation view of an alternative embodiment of a base and outer C-shaped track portion of the dual C-arm gantry.

Turning now to FIGS. 1A–6E, a dual C-arm angiographic device for flat panel x-ray receptor ("dual C-arm gantry") 20 will now be described. The dual C-arm gantry 20 is meant to be located at the side of a patient support table 22, and includes a base 24 attached to the floor 26; an outer C-shaped track 28 non-movably attached to the base 24; and a crawler carriage 30 that moves along the outer track 28. Additionally, an inner C- or U-shaped instrument bracket ("inner C-arm") 32, concentric with respect to the outer track 28, is pivotally or rotatably attached to the crawler carriage 30, at a pivot point 34 circumferentially offset from where the carriage 30 is attached to the outer track 28. The inner C-arm 32 is configured to rotate ±180°, while the crawler carriage 30 can move ±90° (with respect to the inner C-arm in a vertical, 0° position, as shown in FIG. 1B) along the outer track 28. This, in combination with the circumferentially-offset inner C-arm 32 and the particular positioning of the outer track 28 (i.e., the outer track is positioned "off-vertical"), provides true spherical angulation, no image rotation, and minimal interference with clinical use patterns.

FIGS. 1A–3 best show the base 24 and outer C-shaped track 28. The base 24 is a compact stand or support member that holds and supports the outer track 28. For this purpose, one side of the base 24 may be curved or contoured, with a portion of the outer track 28 fitting up against the curved section (see FIG. 1 D). Alternatively, as shown in the drawings, one side of the base may define a curved surface that extends all the way along the entire length of the outer track 28. This is useful for more securely supporting the outer track and for providing an interior space for drive components, as discussed further below. The base can be non-movably attached to the floor 26, or it can be attached to the floor via a floor roller carriage-40, which allows the base to move towards and away from the patient support table 22 (sixteen inches or so of travel is usually suitable) for patient loading, and for purposes of moving the point of intersection of the x-ray beam and table.

For clinical use, the dual C-arm gantry 20 is positioned to the side of the patient support table 22. This gives doctors and other medical personnel full access to the head-end of the table and to one complete side of the patient. Also, there are no parts that sweep radially along the floor, as would interfere with equipment or medical personnel. As should be appreciated, the patient support table 22 is shown for purposes of scale and for indicating how the dual C-arm gantry is meant to be positioned during use (the dual C-arm gantry lies to the side of the table, with the table thereby lying generally normal to the dual C-arm gantry proximate/underneath the gantry's isocenter). The table 22 shown in the drawings is not meant to be a component of the present invention per se, since many different tables could be used.

The outer track 28 is non-movably connected to the base 24, and, as mentioned above and as shown in the drawings, is generally C-shaped, or, more precisely, is generally in the shape of a semi-circle. The outer track 28 has parallel side slots 42 or the like for slidably engaging complementary features on the crawler carriage 30 (i.e. the crawler carriage 30 slides along the outer track 28, but cannot become radially detached from it in normal use), as well as an interior space 44 along its length for accommodating drive elements (as discussed below).

Figure 2:
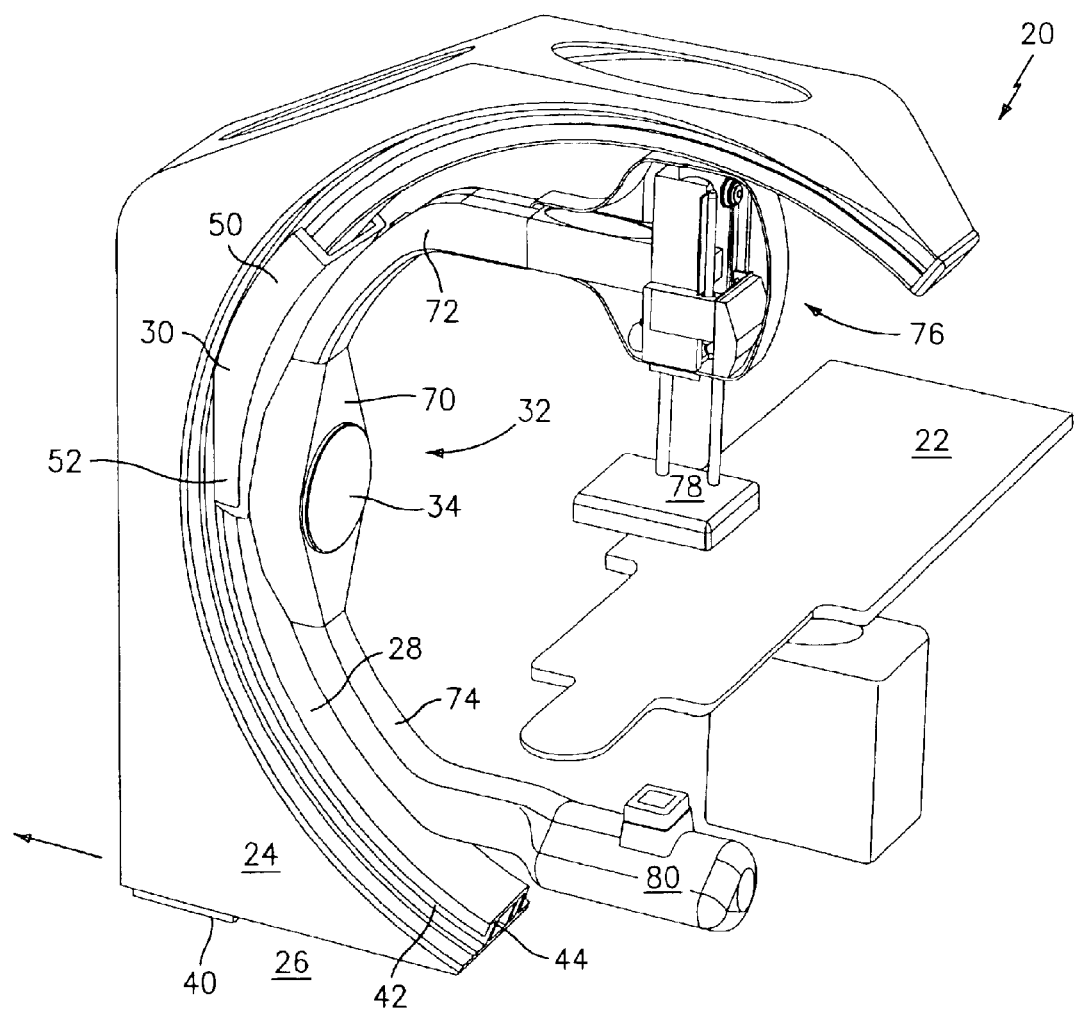
FIG. 2 is a second perspective view of the dual C-arm gantry.
Figure 3:
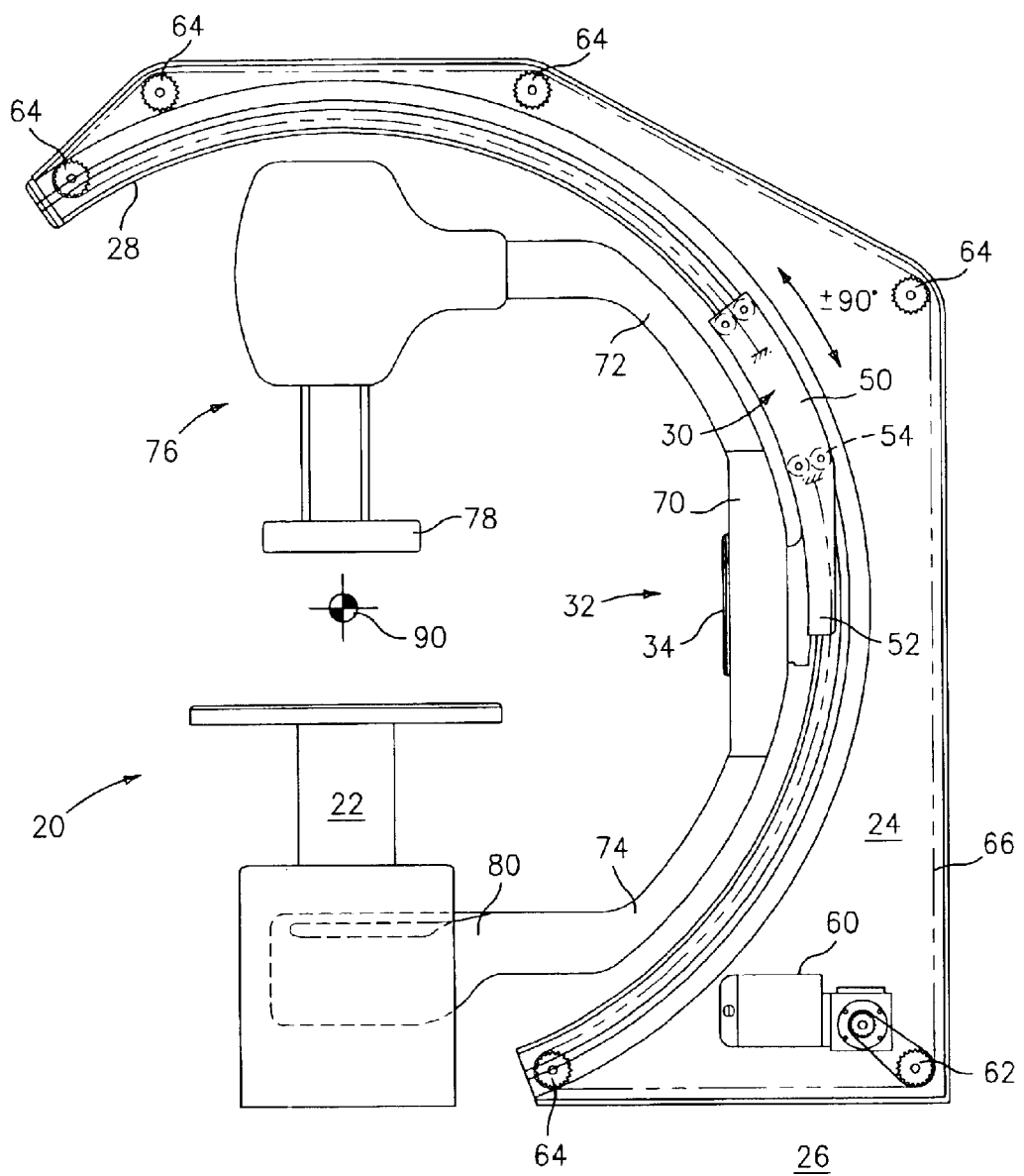
FIG. 3 is a side elevation view of the dual C-arm gantry, showing internal operation of a crawler carriage portion of the dual C-arm gantry.

The crawler carriage 30, with reference to FIGS. 2 and 3 in particular, comprises a sheath-like carriage base 50 and an extension 52 attached to the carriage base. The carriage base and extension are both curved to generally fit against the outer track 28. The carriage base 50 has a plurality of wheels 54, tabs, or other features for slidably engaging the outer track 28. Also, although the extension 52 slides along the outer track 28, it is not connected to the track 28, and can extend out past the bottom end of the outer track 28. In this sense, the extension 52 is said to be "circumferentially offset" from the carriage base 50, for purposes discussed further below.

For moving the crawler carriage 30 along the outer track 28, the base 24 and outer track 28 are outfitted with a circuitous drive mechanism ("drive circuit"), as shown in FIG. 3 (note that the crawler carriage does not have a motor or any other active drive components). The drive circuit is located inside the base 24 and track 28, and comprises: an electrically powered motor 60 that turns a drive sprocket 62; a plurality of rollers or idler pulleys 64 positioned at various "inflection" points along the periphery of the base 24; and a drive chain 66. The drive chain 66 is operably connected to the sprocket 62 and idler pulleys 64, and is guided/positioned by the idler pulleys 64 to pass through the interior space 44 of the outer track 28 and to traverse the periphery of the interior of the base 24. One end of the drive chain 66 is connected to the top end of the crawler carriage base 50, and the other end of the drive chain 66 is connected to the bottom end of the crawler carriage base 50.

In use, electricity is supplied to the motor 60, via a standard control circuit or the like (not shown). This causes the drive sprocket 62 to rotate, the chain 66 to move, and the chain to pull the crawler carriage 30 along the outer track 28. For example, from the perspective of FIG. 3, when the drive sprocket 62 is rotated clockwise, the portion of the drive chain 66 immediately above the sprocket is pulled downwards. This movement is translated along the length of the chain via the idler pulleys 64, such that the crawler carriage 30 is pulled upwards along the outer track 28, and the drive chain "circuit" is advanced clockwise. Counterclockwise movement of the drive sprocket 62 pulls the crawler carriage 30 down along the outer track. Of course, the crawler carriage and outer track may be provided with complementary features for ensuring the carriage stops when it reaches either end of the outer track, regardless of whether the motor is still running. Alternatively, or in addition, the position of the crawler carriage may be monitored by a control circuit to ensure the motor stops when the carriage reaches either end of the outer track.

Besides using a drive circuit, as described above, the crawler carriage 30 could be moved along the outer track 28 by other means. For example, a "linear" drive could be used, which would comprise: a chain or belt positioned inside the outer track and affixed at either end to the top and bottom ends of the outer track; and a motor, drive sprocket, and idler pulley(s) attached to the crawler carriage and operably connected to the chain or belt. In use, the motor on the crawler carriage would turn the sprocket, with the crawler carriage thereby effectively pulling itself up and down the chain or belt.

The inner C-arm 32, as mentioned above, is generally C-shaped, with a central base 70 and "upper" and "lower" curving arms 72, 74, respectively. A detector/counterweight housing 76 and a-flat-panel x-ray receptor 78 are attached to the end of the upper arm 72, while an x-ray tube and collimator unit 80 is attached to the end of the lower arm 74. It should be noted that the inner C-arm 32 does not slide in its pivot mount at all, i.e., it does not slide with respect to the crawler carriage. This results in lower manufacturing and parts costs, because there is no need for a precision-machined "C" radius, and because rolling contact on the inner C-arm is not required. Also, the lack of a sliding surface facing patients on the inner C-arm increases sterility, since it is easier to clean and to keep clean.

Figure 4A:
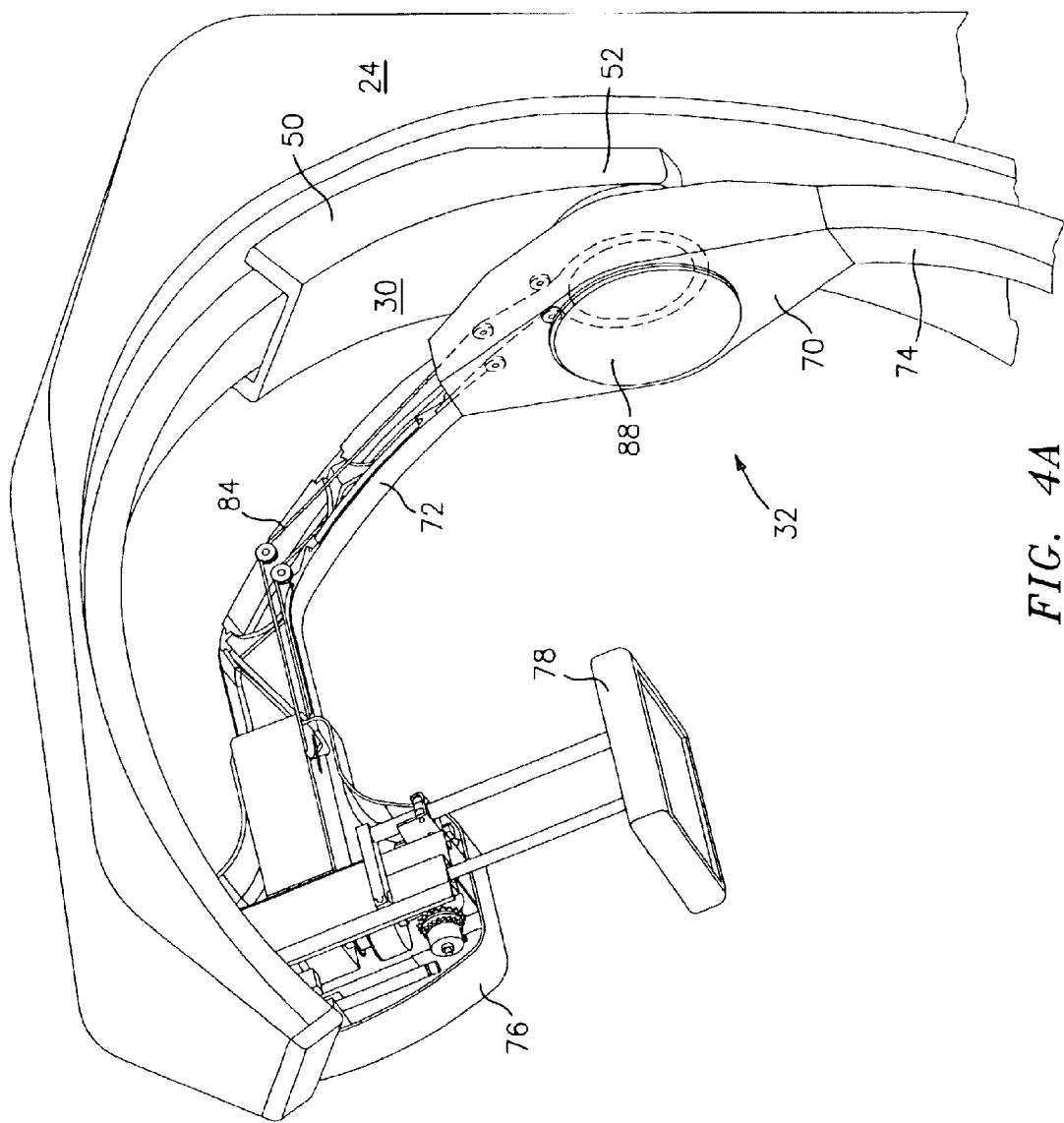
FIGS. 4A–4C are perspective and side elevation views, partially in cutaway, showing the rotational operation of an inner C-arm portion of the dual C-arm gantry.
Figure 4B:
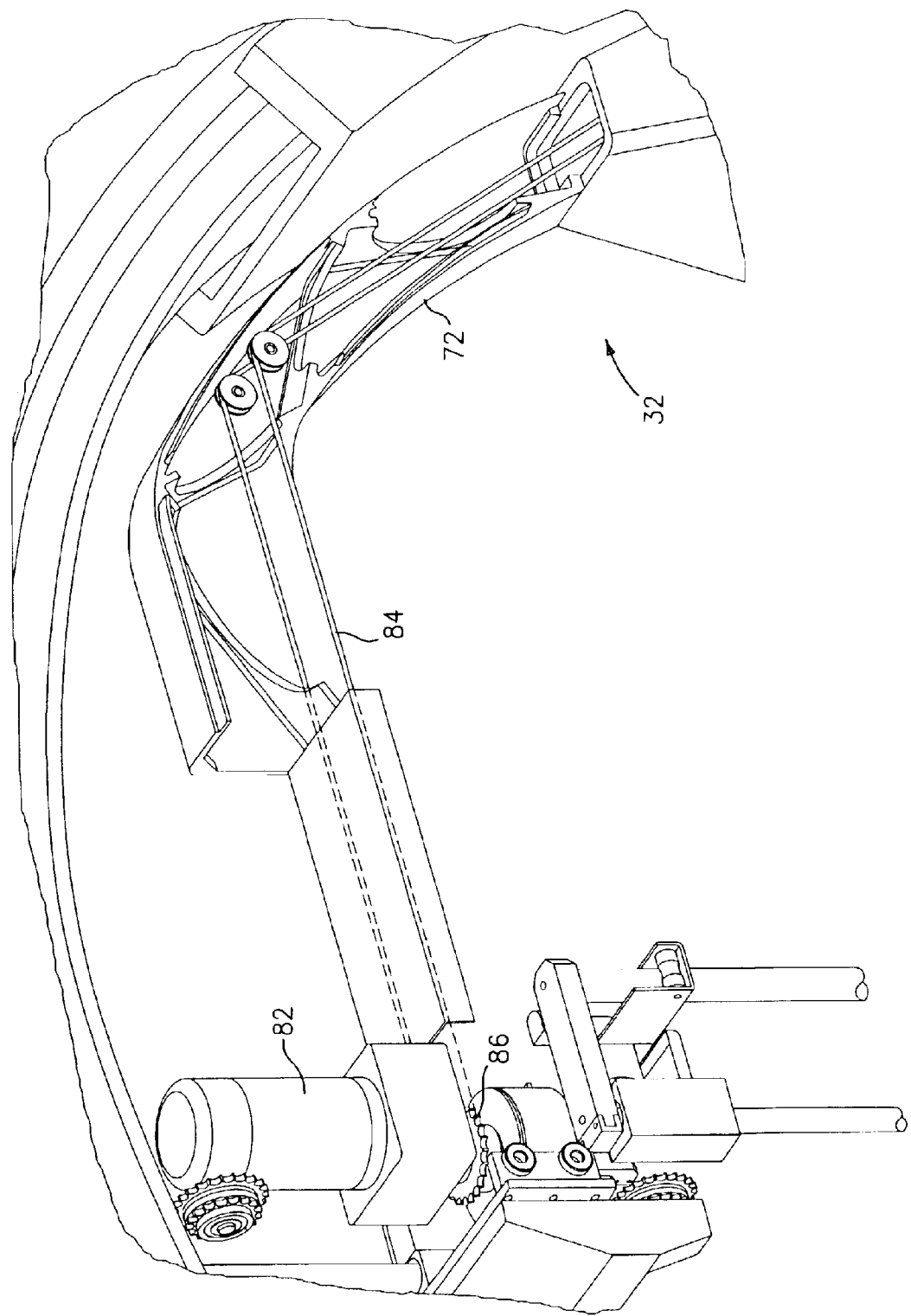
Figure 4C:
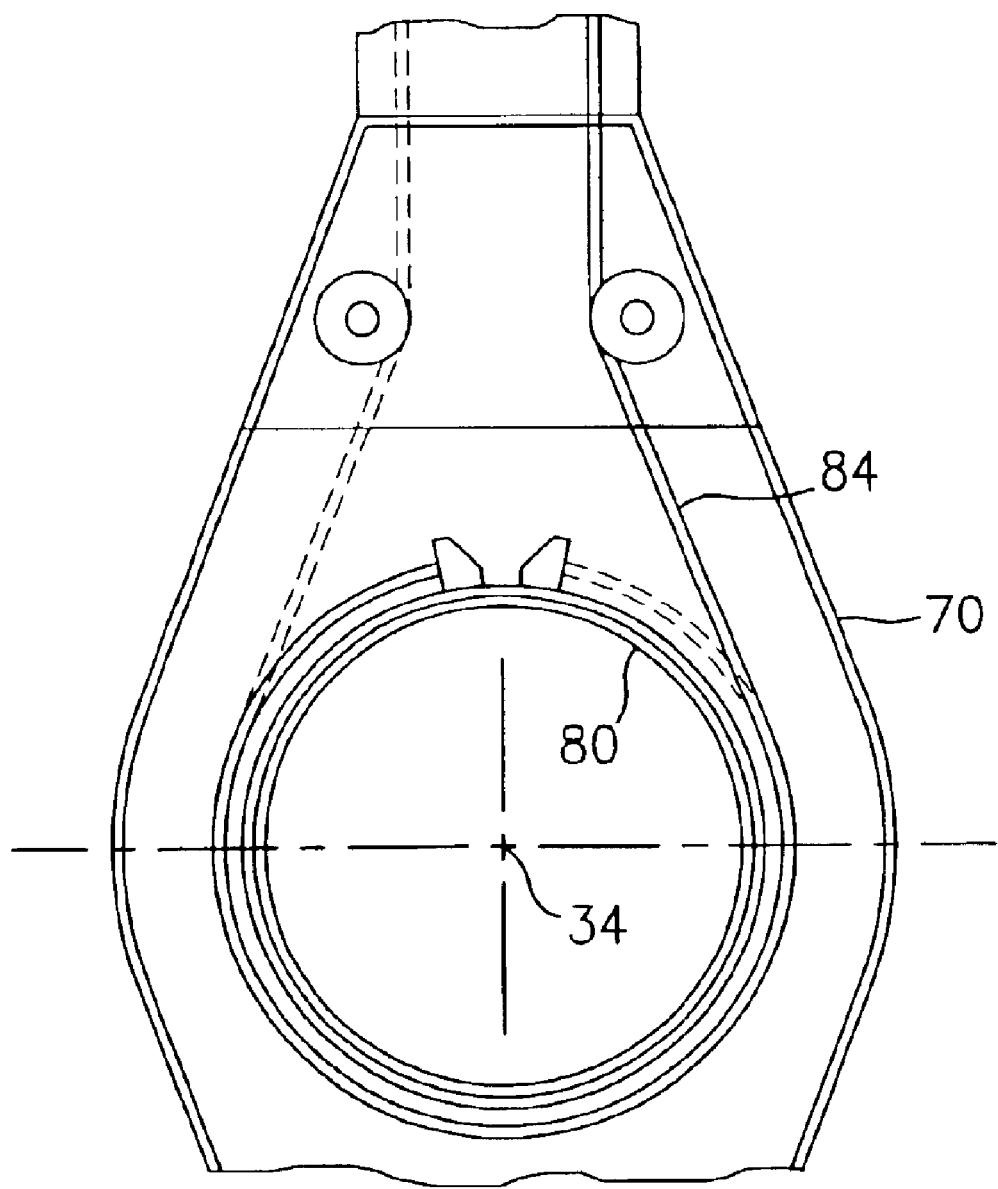

The inner C-arm is capable of ±180° rotation with respect to the outer track 28. For this purpose, as shown in FIGS. 4A–4C, the inner C-arm 32 has a rotation drive unit. The rotation drive unit includes an inner C-arm drive gearmotor and clutch unit 82, and an inner C-arm rotation drive cable or chain 84. The gearmotor/clutch unit 82 is located in the detector/counterweight housing 76, for purposes of helping to offset the weight of the x-ray tube and collimator unit 80 on the other end of the inner C-arm 32. The drive cable or chain 84 operably wraps around a drive element 86 (gear or sprocket, drive wheel, etc.) driven by the gearmotor/clutch unit 82, and extends down through a hollow interior portion of the upper arm 72 to the inner C-arm's central base 70 (the drive chain is guided by idler pulleys or other guide elements). The central base 70 has an interior hub or drum 88, attached to the base, that is coaxial with the inner C-arm pivot point 34, as shown in FIG. 4C. One end portion of the drive cable or chain 84 is wound around the drum 88 in one direction (e.g., clockwise), while the other end portion of the drive cable 84 is would around the drum 88 in the other direction (e.g., counterclockwise). Both ends of the drive cable 84 are affixed to the drum 88. In use, operation of the gearmotor/clutch unit 82 moves the drive cable 84, causing one of the cable end portions to unwind from the drum 88. As the cable unwinds, the drum is forced to rotate, causing the entire inner C-arm 32 to rotate as well. Controlled power may be provided to the gearmotor/clutch unit 82 via an electronic control unit or other controls (not shown), via electrical cables (not shown) extending from the base 24, through the outer track 28 and crawler carriage 30, and into the inner C-arm 32.

Figure 5A:
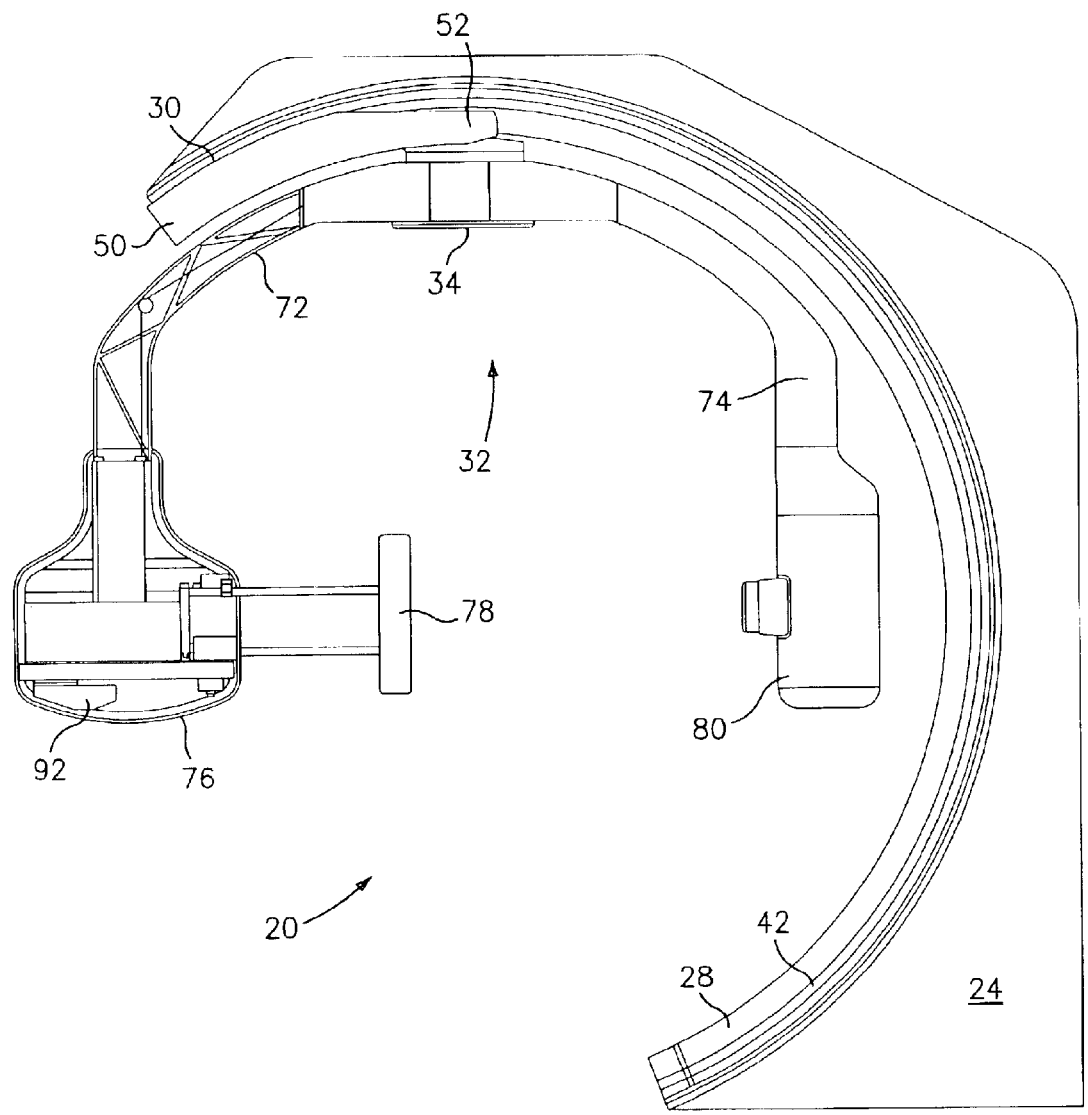
FIGS. 5A and 5B are side elevation views of the dual C-arm gantry, showing "top" and "bottom" crawler carriage positions, respectively.
Figure 5B:
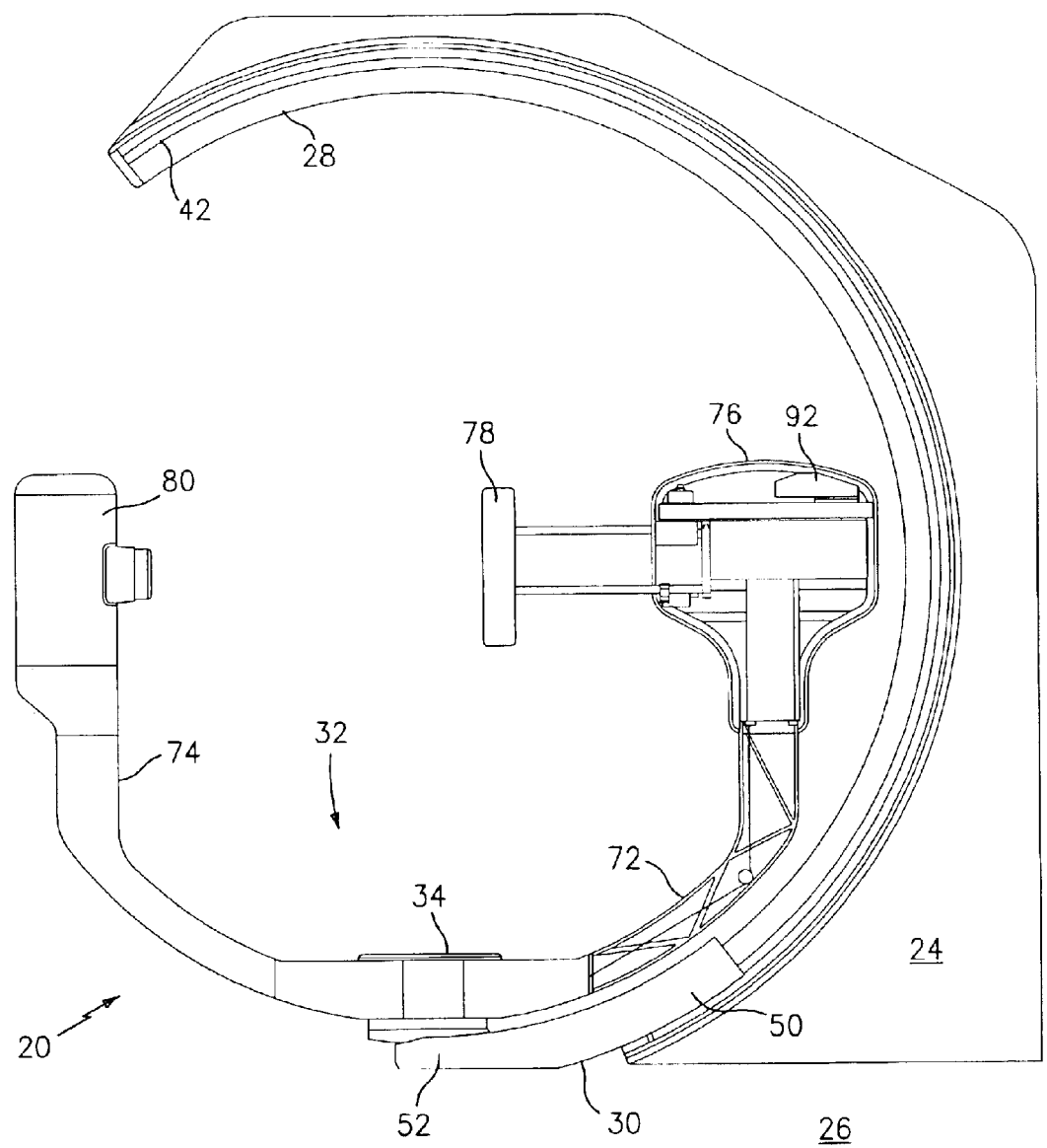

Turning now to FIGS. 1B and 5A–5D, an explanation of the particular geometrical/spatial arrangement of the dual C-arm gantry 20 will now be given. As mentioned above, the inner C-arm 32 is capable of ±90° transverse (across or around a patient's long axis) coverage, by moving the crawler carriage 30 from one end of the outer track 28 (FIG. 5A) to the other (FIG. 5B). For this purpose, the length of the outer track 28 is just sufficient to allow ±90° angulation from vertical of the x-ray beam, in a transverse (across the patient) sense.

Also, to enable the outer track 28 to be placed in a location where it interferes the least with clinical use patterns, the inner C-arm pivot point 34, located on the extension portion 52 of the carriage 30, is circumferentially offset from where the crawler carriage base 50 slides along the outer track. This allows the outer track 28 to be "rotated past vertical," by which it is meant that the bottom end of the outer track is offset or angled by about 20° to about 30° or so (as shown in FIG. 5D) past a "0-degree," more strictly vertically-oriented position (as shown in FIG. 5C). In this position, while the outer track 28 is still generally vertically oriented, the bottom part of the dual C-arm gantry does not extend to much of an extent under the table 22 (if at all), and the overhead part of the outer track 28 is truncated at, or above, head height, eliminating possible interference on the side of the patient away from the dual C-arm gantry. Thus, when the crawler carriage 30 reaches the top end of the outer track 28, the inner C-arm 32 is at its horizontally-oriented ±90° position (with the inner C-arm generally lying above the axis defined by the x-ray source and receptor), as shown in FIG. 5A, even though the crawler carriage is past the ±90° (12 o'clock) position. Also, when the crawler carriage 30 reaches the bottom end of the outer track 28, the inner C-arm 32 is at its horizontally-oriented −90° position (with the inner C-arm generally lying below the axis defined by the x-ray source and receptor), as shown in FIG. 5B. This is true even though the outer track does not extend as far as the −90° (6 o'clock) position, by virtue of the extension portion 52 of the crawler carriage 30 projecting out past the end of the outer track.

This geometrical configuration (non-sliding inner C-arm, circumferentially-offset pivot, floor mounted base) has the advantage of inherently not rotating the flat panel x-ray receptor, regardless of angle or compound angles used, and is very stable due to the floor mount. Also, the projection angles are true geometric angles as measured, as if these were concentric spheres, or a parallelogram. This is opposed to other, "sliding" constructions, where multiple angles interact, and complicated mathematical functions are employed to translate the interactive motions into angles that the medical personnel can comprehend and that are referenced to the patient axis.

For rotating the inner C-arm about its pivot point and for easily moving the inner C-arm around the outer track, and to eliminate imbalance and/or untoward stresses or forces on the dual C-arm gantry, the crawler carriage 30 and inner C-arm 32 are balanced about the isocenter 90 of the dual C-arm gantry 20 to the extent possible (perfect balance may not be possible because of space constraints). The isocenter is the point of intersection of a longitudinal axis between the flat panel x-ray receptor 78 and the x-ray tube and collimator unit 80, and a longitudinal axis defined by the inner C-arm pivot point 34. For maximizing balance, a number of strategies are utilized. These include positioning heavier components at locations where they balance with other components, and a counterweight system which allows the use of a flat panel x-ray receptor and eliminates the need for an image intensifier tube. In particular, flat panel x-ray receptors, which typically use a matrix of selenium-based pixels for detecting x-rays, are very light weight and are difficult to balance against the opposite, much heavier x-ray tube and collimator.

To elaborate, both ends of the inner C-arm 32 are configured to weigh about the same, such that the inner C-arm 32 is balanced about its traveling pivot point 34. Since the x-ray tube and collimator unit 80 is much heavier than the flat panel x-ray receptor 78, this is accomplished by: (i) mounting the inner C-arm drive gearmotor and clutch unit 82 in the detector/counterweight housing 76; and (ii) attaching a counterweight 92 to the detector/counterweight housing 76 (basically, the weight of the counterweight, flat panel receptor 78, and related components is approximately the same as the weight of the x-ray tube and collimator unit 80). To the extent possible, the counterweight and drives are "pushed outwards" (i.e., located outboard), as far away from the crawler carriage 30 as possible, to help offset and balance the weight of the crawler carriage and the inner C-arm's eccentricity about the isocenter 90.

Figure 6A:
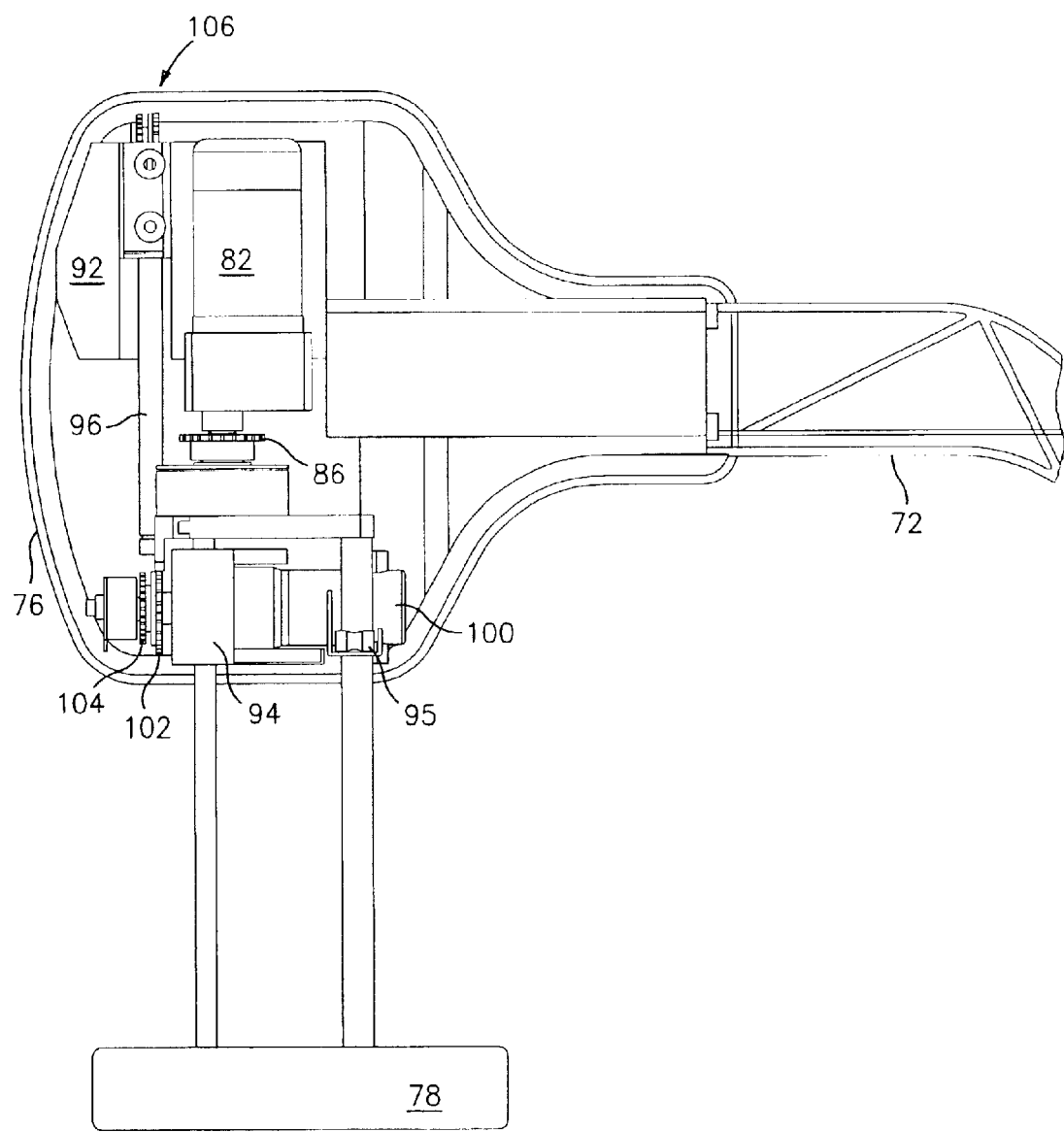
Figure 6B:
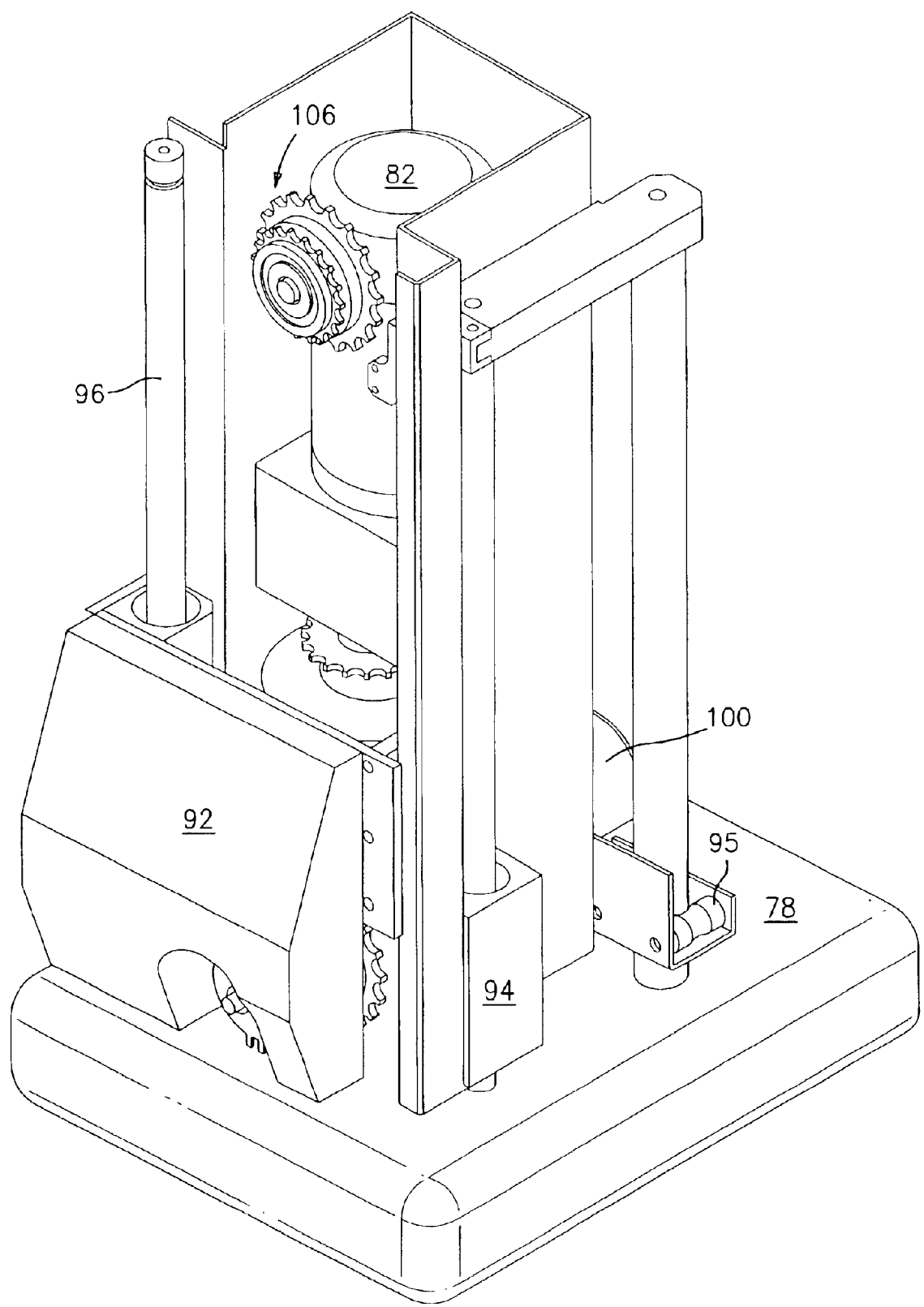
Figure 6C:
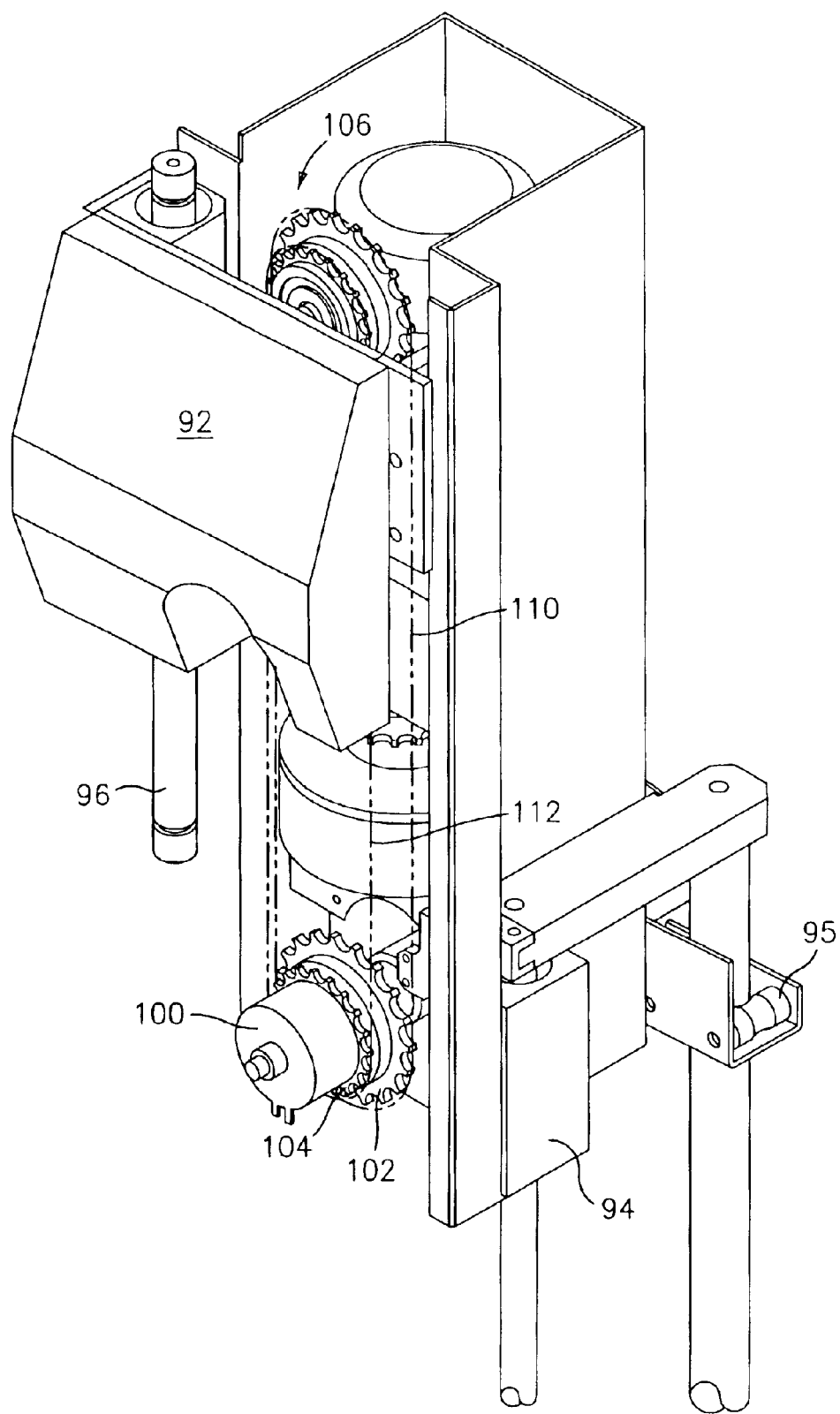

FIGS. 6A–6E show a mechanism for moving the x-ray receptor 78 in and out along the x-ray beam axis (to accommodate different sizes of patients), while still preserving an optimal counterbalance. First, the flat panel x-ray detector 78 is movably attached to the detector/counterweight housing 76, such that it can be moved to a fully extended position (e.g., +12"), where the source-to-image distance ("SID") is at a minimum, as shown in FIGS. 6A and 6C, and to a fully retracted position, where the SID is at a maximum, as shown in FIG. 6B. The x-ray receptor 78 may be supported and guided by linear bearings 94 and/or guide rollers 95. Also, the counterweight 92 is movably attached to the detector/counterweight housing 76 via a counterweight rail 96.

For moving the counterweight and x-ray receptor, a variable-SID drive motor and clutch unit 100 is attached to the detector/counterweight housing 76. The output of the SID drive unit 100 is attached to a detector drive sprocket 102 and a counterweight drive sprocket 104, which is coaxial with the detector drive sprocket 102. The two drive sprockets 102, 104 are provided in a non-integer gear ratio, i.e., different sizes, with the detector gear 102 being the larger of the two. Further, a pair of idler sprockets 106 are rotatably attached to the detector/counterweight housing 76 towards its top (e.g., away from the sprockets 102, 104). The idler sprockets are aligned with and respectively match the drive sprockets 102, 104. Also, a receptor drive chain 110 and a counterweight drive chain 112 are operably disposed about the detector drive sprocket 102 and the counterweight drive sprocket 104, respectively, and their corresponding idler sprockets 106.

In use, the x-ray receptor 78 is attached to the receptor drive chain 110 on one side of a longitudinal axis defined by the sprockets 102, 104, 106, and the counterweight 92 is attached to the counterweight drive chain 112 on the other side. This is shown schematically in FIGS. 6D and 6E. When the SID drive unit 100 is operated (e.g., to move the x-ray receptor 78 from its retracted position to its extended position), the detector drive sprocket 102 and counterweight drive sprocket 104 are rotated, moving the drive chains 10, 112 around the idler sprockets 106. Since the x-ray receptor 78 is attached to the "side" of its drive chain 110 which moves in one direction, while the counterweight 92 is attached to the opposite "side" of its drive chain 112, which moves in the other direction, the x-ray receptor 78 moves "downwards" away from the detector/counterweight housing 76, while the counterweight 92 moves in the opposite direction. This maintains a fixed center of gravity for the detector/counterweight housing.

To provide enough weight to balance the x-ray tube and collimator unit 80, the counterweight 92 is heavier than the x-ray receptor 78. Accordingly, to maintain a set center of gravity, the counterweight 92 travels a smaller distance than the x-ray receptor 78 when the two are moved towards or away from one another by the SID drive unit 100. This is accomplished via the differential sprocket size. More specifically, when the SID drive unit 100 is operated, the drive sprockets 102, 104, being coaxial, are subjected to the same degree of angular movement (rotation). However, since the counterweight drive sprocket 104 is smaller than the detector drive sprocket 102, the counterweight drive chain 112 (and counterweight 92) is moved a shorter distance than the receptor drive chain 110 and x-ray receptor 78 (compare FIG. 6D to FIG. 6E).

As should be appreciated, the x-ray receptor 78 may be manually positioned via disengagement of the SID drive unit clutch, or the x-ray receptor 78 may be solely manually positionable by eliminating the SID drive unit 100 altogether, but keeping the various sprockets and drive chains. Of course, some sort of "braking" device would need to be provided to enable a user to hold the x-ray receptor and counterweight in place once positioned at the desired location.

By virtue of the inner C-arm's configuration described above (the outboard counterweight 92 and all the drive components located in the detector/counterweight housing 76), the bulk of the inner C-arm's weight is positioned with respect to the C-arm's "C-structure" moment arm so as to help balance the entire "C" assembly moment around the isocenter 90, which reduces forces that may otherwise cause the inner C-arm to crawl (i.e., if all weights have a sum of moments that cancel each other, the effort to move along the outer track is essentially zero—it is simply a rotation around the center of gravity). This effect is further enhanced in the present design by the off-axis portion of the inner C-arm (specifically, the inner C-arm base 70 and surrounding area) being made as light as possible, e.g., no drive motors or counterweights.

As mentioned above, the dual C-arm gantry 20 will typically be used in conjunction with a standard electronic control unit or circuit (not shown), similar to those used on other x-ray support devices. The electronic control unit may perform one or more of the following functions: (i) providing power to the electrically-operated portions of the dual C-arm gantry (motors, clutches, flat panel receptor, x-ray tube and collimator); (ii) providing control signals to the electrically-controllable portions of the dual C-arm gantry, including the x-ray tube and collimator; (iii) providing a user interface and/or controls for allowing a user to operate the dual C-arm gantry; and (iv) processing, displaying, storing, and/or transmitting images (sensed information) received by the flat panel receptor. The control unit may be implemented as part of, or used in conjunction with, a computer (e.g., images received by the flat panel receptor may be transmitted to a computer for processing, display, and/or storage).

For connecting the electronic control unit to the electrically-controlled and/or -operated portions of the dual C-arm gantry, various electrical leads (not shown) may be wound through the interior of the dual C-arm gantry, e.g., into the base 24, through the outer track 28, through the carriage 30 and into the inner C-arm 32. Leads can also be attached externally.

According to the design of the base 24 and outer track 28, e.g., as shown in FIG. 1B and 1D, the lower portion of the outer track 28 is held and supported by the base 24. This greatly enhances the overall stability of the dual C-arm gantry 20, and facilitates achieving balance (or near balance) about the isocenter 90.

In another sense, the present invention can be characterized as having: support means (the base 24) for stably, non-movably supporting at least a lower portion of the outer track 28 against the floor 26; medical imaging device support means (inner arm 32) for supporting the x-ray source 80 and receptor 78 in an opposed relationship (i.e., across from one another); and a medical imaging device positioning means (the carriage 30), movable along the outer track, for positioning the inner arm 32 at a 0° position, where an axis defined by (i.e., extending between) the x-ray source and receptor is vertically oriented (FIGS. 2 & 3), and at ±90° positions (FIGS. 5A & 5B), where the axis is horizontally oriented. Further, while the medical imaging device support means is rotatably attached to the medical imaging device positioning means, it is non-sliding, thereby achieving spherical angulation about the isocenter 90 of the gantry 20 without image rotation.

Although the base and outer track have been described as comprising separate elements, it should be noted that the base and outer track could be provided as a single unit, e.g., a base with an integral outer track where the base defines a C-shaped surface with features for slidably engaging the crawler carriage. Accordingly, where the present invention is characterized as having the outer track "attached" to the base, it should be appreciated that this encompasses both a separate base and outer track connected to one another and a base that defines or includes an integral outer track.

Also, although the dual C-arm gantry of the present invention has been illustrated as having various motors for movement of the crawler carriage and inner C-arm, one of ordinary skill in the art will appreciate that the motors could be replaced with manual control/movement elements, such as hand cranks, without departing from the spirit and scope of the invention.

Although the dual C-arm gantry of the present invention has been generally illustrated as being for use with an x-ray receptor and x-ray source and collimator, it should be appreciated that the dual C-arm gantry could be used for positioning different types of medical imaging devices, e.g., of the type comprising an imaging source and an imaging receptor.

Further, although the dual C-arm gantry of the present invention has been illustrated as having a "rotated past vertical" outer track, one of ordinary skill in the art will appreciate that the outer track could be more vertically oriented, as shown in FIG. 5C, with an appropriately configured carriage, without departing from the spirit and scope of the invention (e.g., in situations where a minimum of interference with clinical use patterns is not needed).

Although the crawler carriage has been illustrated as fitting over the outer track, it should be appreciated that the carriage could also be a curved member that slides or otherwise moves along an interior, slot-like groove provided in the outer track, without departing from the spirit and scope of the invention.

Since certain changes may be made in the above dual C-arm angiographic device for flat panel x-ray receptor, without departing from the spirit and scope of the invention herein involved, it is intended that all of the subject matter of the above description or shown in the accompanying drawings shall be interpreted merely as examples illustrating the inventive concept herein and shall not be construed as limiting the invention.

Having thus described the invention, what is claimed is:

1. A support and positioning apparatus for medical imaging devices comprising:
   a. a base configured for attachment to a floor;
   b. a generally vertically oriented, curved outer track non-movably attached to the base, said base supporting at least a lower portion of the outer track;
   c. a carriage movable along the outer track; and
   d. a curved inner arm rotatably attached to the carriage and generally concentric with the outer track, said inner arm supporting a medical imaging device, wherein:
   e. the outer track and inner arm are configured for ±90° transverse coverage of the inner arm and medical imaging device, from a 0°, vertical position of the inner arm, across an axis normal to the gantry and extending through an isocenter of the gantry, such that the medical imaging device can be spherically angulated about a patient; and
   f. the inner arm is non-slidably attached to the carriage, thereby eliminating image rotation of the medical imaging device and enhancing sterility.

2. The support and positioning apparatus of claim 1 wherein:
   a. the outer track is rotated past vertical;
   b. the carriage comprises: a carriage base movably engaging the outer track; and an extension connected to the carriage base and circumferentially offset from the carriage base; and
   c. the inner arm is rotatably attached to the extension, and the extension projects out past the lower end of the outer track when the carriage is moved to the lower end of the outer track, such that the support and positioning apparatus can be positioned to the side of a patient support table, thereby reducing interference with clinical use patterns without losing spherical angulation capability.

3. The support and positioning apparatus of claim 1 wherein:
   a. the inner arm comprises: an inner arm base rotatably attached to the carriage; and upper and lower curving arm portions attached to the inner arm base;
   b. the medical imaging device comprises: an x-ray source attached to an end of the lower curving arm portion; and a flat panel x-ray receptor attached to an end of the upper curving arm portion; and
   c. the support and positioning apparatus further comprises a counterweight mechanism attached to the upper curving arm portion for counterbalancing the x-ray source.

4. The support and positioning apparatus of claim 3 further comprising an inner arm rotation drive unit, wherein: the inner arm rotation drive unit is attached to the end of the upper curving arm portion of the inner arm to help counterbalance the x-ray source; and the inner arm rotation drive unit operably engages a hub portion of the inner arm base for controllably rotating the inner arm.

5. The support and positioning apparatus of claim 1 further comprising at least one counterweight mechanism attached to the inner arm for facilitating balance about an isocenter of the support and positioning apparatus.

6. A support and positioning apparatus for medical imaging devices comprising:
   a. a base configured for attachment to a floor and having a curved outer track non-movably attached thereto;
   b. a carriage movable along the outer track; and
   c. a non-sliding, curved inner arm rotatably attached to the carriage and generally concentric with the outer track, said inner arm supporting a medical imaging device; wherein the outer track and carriage are mutually configured for movement of the carriage between: a first position, wherein the inner arm is horizontally-oriented and lies generally below an axis defined by the medical imaging device; a second position, wherein the inner arm is vertically-oriented; and a third position, wherein the inner arm is horizontally-oriented and lies generally above the axis defined by the medical imaging device; such that the medical imaging device can be spherically angulated about a patient without image rotation.

7. The support and positioning apparatus of claim 6 wherein:
   a. the outer track is rotated past vertical; and
   b. the carriage comprises: a carriage base movably engaging the outer track; and an extension connected to the carriage base and circumferentially offset from the carriage base, wherein:
   c. the inner arm is rotatably attached to the extension and the extension projects out past a lower end of the outer track when the carriage is at the carriage's first position, such that the support and positioning apparatus can be positioned to the side of a patient support table to reduce interference with clinical use patterns without losing spherical angulation capability.

8. The support and positioning apparatus of claim 6 wherein:
   a. the inner arm comprises: an inner arm base rotatably attached to the carriage; and upper and lower curving arm portions attached to the inner arm base;
   b. the medical imaging device comprises: an x-ray source attached to an end of the lower curving arm portion;

and a flat panel x-ray receptor attached to an end of the upper curving arm portion; and c. the support and positioning apparatus further comprises a counterweight mechanism attached to the upper curving arm portion for counterbalancing the x-ray source.

9. The support and positioning apparatus of claim 8 further comprising an inner arm rotation drive unit, wherein: the inner arm rotation drive unit is attached to the end of the upper curving arm portion of the inner arm to help counterbalance the x-ray source; and the inner arm rotation drive unit operably engages a hub portion of the inner arm base for controllably rotating the inner arm.

10. The support and positioning apparatus of claim 6 further comprising at least one counterweight mechanism attached to the inner arm for facilitating balance about an isocenter of the support and positioning apparatus.

11. The support and positioning apparatus of claim 6 wherein: the outer track is generally vertically oriented; and the base supports at least a lower portion of the outer track, thereby increasing stability of the support and positioning apparatus.

12. A support and positioning apparatus for medical imaging devices comprising:
   a. a base attached to a floor and positioned to the side of a patient support table;
   b. a generally vertically oriented, curved outer track non-movably attached to the base, wherein:
      i. the base supports at least a lower portion of the outer track; and
      ii. the outer track is rotated past vertical to arch up over the patient support table but not to extend substantially underneath the patient support table, thereby reducing interference with clinical use patterns;
   c. a carriage comprising: a carriage base movably engaging the outer track; and an extension connected to the carriage base and circumferentially offset from the carriage base; and
   d. a curved inner arm rotatably attached to the extension portion of the carriage and generally concentric with the outer track, said inner arm supporting a medical imaging device, wherein:
   e. the inner arm and outer track are configured for ±90° transverse coverage of the inner arm, from a 0°, vertical position of the inner arm, across an axis normal to the support and positioning apparatus and extending through an isocenter of the support and positioning apparatus; and
   f. the inner arm is non-slidable, thereby eliminating image rotation of the medical imaging device.

13. The support and positioning apparatus of claim 12 wherein:
   a. the inner arm comprises: an inner arm base rotatably attached to the extension portion of the carriage; and upper and lower curving arm portions attached to the inner arm base;
   b. the medical imaging device comprises: an x-ray source attached to an end of the lower curving arm portion; and a flat panel x-ray receptor attached to an end of the upper curving arm portion; and
   c. the support and positioning apparatus further comprises a counterweight mechanism attached to the upper curving arm portion for counterbalancing the x-ray source.

14. The support and positioning apparatus of claim 13 further comprising an inner arm rotation drive unit, wherein: the inner arm rotation drive unit is attached to the end of the upper curving arm portion of the inner arm to help counterbalance the x-ray source; and the inner arm rotation drive unit operably engages a hub portion of the inner arm base for controllably rotating the inner arm.

15. The support and positioning apparatus of claim 12 further comprising at least one counterweight mechanism attached to the inner arm for facilitating balance about an isocenter of the support and positioning apparatus.

16. A medical imaging device gantry comprising:
   a. a curved, outer track;
   b. a base non-movably supporting the outer track;
   c. a carriage movable along the outer track; and
   d. a non-sliding, curved inner arm rotatably attached to the carriage and configured to support a medical imaging device, wherein the outer track and inner arm are configured for ±90° transverse coverage of the inner arm and medical imaging device, from a 0° position of the inner arm, across an axis normal to the gantry and extending through an isocenter of the gantry.

17. A medical imaging device gantry comprising:
   a. a base configured for attachment to a floor;
   b. a generally vertically oriented, curved outer track non-movably attached to the base, said base supporting at least a lower portion of the outer track;
   c. a carriage movable along the outer track; and
   d. a non-sliding, curved inner arm rotatably attached to the carriage and configured to support a medical imaging device, wherein the inner arm and outer track are configured for ±90° transverse coverage of the inner arm, from a 0°, vertical position of the inner arm, across an axis normal to the gantry and extending through an isocenter of the gantry.

18. The gantry of claim 17 wherein:
   a. the outer track is rotated past vertical;
   b. the carriage comprises: a carriage base movably engaging the outer track; and an extension connected to the carriage base and circumferentially offset from the carriage base; and
   c. the inner arm is rotatably attached to the extension and the extension projects out past a lower end of the outer track when the carriage is moved to the lower end of the outer track, such that the gantry can be positioned to the side of a patient support table to reduce interference with clinical use patterns.

19. The gantry of claim 17 wherein:
   a. the inner arm comprises: an inner arm base rotatably attached to the carriage; and upper and lower curving arm portions attached to the inner arm base; and
   b. the gantry further comprises:
      i. a medical imaging device comprising: an x-ray source attached to an end of the lower curving arm portion; and a flat panel x-ray receptor attached to an end of the upper curving arm portion; and
      ii. a counterweight mechanism attached to the upper curving arm portion for counterbalancing the x-ray source.

20. A medical imaging device gantry comprising:
   a. a curved, generally vertically oriented outer track;
   b. support means for stably, non-movably supporting at least a lower portion of the outer track against a floor;
   c. a carriage movable along the outer track; and
   d. a non-sliding, curved inner arm rotatably attached to the carriage and configured to support a medical imaging device, wherein the carriage is movable from a 0° position, where the inner arm is vertically oriented, to ±90° positions, where the inner arm is horizontally oriented, thereby achieving spherical angulation about an isocenter of the gantry.

21. A medical imaging device gantry comprising:
a. a base; a generally vertically oriented, curved outer track non-movably attached to the base; a carriage moveable along the outer track; and a curved inner arm rotatably attached to the carriage and configured to support a medical imaging device, wherein:
b. the gantry is positioned to the side of a patient support table with the base attached to a floor and supporting at least a lower portion of the outer track, thereby leaving a head end of the table clear and reducing interference with clinical use patterns; and
c. the inner arm is non-slidable with respect to the carriage, and the inner arm is a unitary member having no portions that slide with respect to one another, thereby enhancing sterility and eliminating image rotation.

22. A medical imaging device gantry comprising:
a. a curved, generally vertically oriented outer track;
b. support means for stably, non-movably supporting at least a lower portion of the outer track against a floor;
c. medical imaging device support means for supporting a medical imaging device source and a medical imaging device receptor in an opposed relationship;
d. medical imaging device positioning means, movable along the outer track, for positioning the medical imaging device support means at a 0° position, where an axis defined by the medical imaging device source and receptor is vertically oriented, and at ±90° positions, where the axis defined by the medical imaging device source and receptor is horizontally oriented, wherein: the medical imaging device support means is non-slidably rotatably attached to the medical imaging device positioning means for spherical angulation about an isocenter of the gantry without image rotation.

* * * * *

UNITED STATES PATENT AND TRADEMARK OFFICE
CERTIFICATE OF CORRECTION

PATENT NO. : 6,789,941 B1
DATED : September 14, 2004
INVENTOR(S) : John K. Grady It is certified that error appears in the above-identified patent and that said Letters Patent is hereby corrected as shown below:

Column 3,
Line 48, change "lube" to -- tube --.
Line 59, change "((he" to -- the --.

Column 5,
Line 32, delete "-" after the word "carriage".
Line 56, insert -- , -- after the word "i.e."

Column 7,
Line 20, change "would" to -- wound --.
Lines 59 and 62, change "± 90°" to -- +90° --.

Column 9,
Line 24, change "10" to -- 110 --.

Column 14,
Line 7, delete "an" after the word "about".

Signed and Sealed this

Eighth Day of February, 2005

JON W. DUDAS
*Director of the United States Patent and Trademark Office*